(12) United States Patent
Lacombe et al.

(10) Patent No.: US 6,533,923 B2
(45) Date of Patent: Mar. 18, 2003

(54) TRIOCTAHEDRAL PHYLLOSILICATES 2:1 OF A STEVENSITE OR KEROLITE TYPE MODIFIED POST-SYNTHESIS, METHOD OF PREPARATION AND USE IN CATALYSIS

(75) Inventors: Sylvie Lacombe, Rueil Malmaison (FR); Véronique Schlussel, Saint Louis (FR); Jacques Baron, Mulhouse (FR); Ronan Le Dred, Riedisheim (FR)

(73) Assignee: Institut Francais du Pétrole, Rueil-Malmaison Cédex (FR)

(*) Notice: Subject to any disclaimer, the term of this patent is extended or adjusted under 35 U.S.C. 154(b) by 52 days.

(21) Appl. No.: 09/745,486

(22) Filed: Dec. 26, 2000

(65) Prior Publication Data

US 2001/0046936 A1 Nov. 29, 2001

(30) Foreign Application Priority Data

Dec. 23, 1999 (FR) .............................. 99 16382

(51) Int. Cl.[7] .......................... C10G 47/02; B01J 21/00; C01B 33/20
(52) U.S. Cl. .................. 208/108; 208/109; 208/111.25; 208/111.35; 423/324; 423/326; 423/327.1; 423/331; 502/63; 502/80
(58) Field of Search ................. 208/108, 109, 208/111.25, 111.35; 423/324, 326, 327.1, 331; 502/63, 80

(56) References Cited

U.S. PATENT DOCUMENTS

| | | | | |
|---|---|---|---|---|
| 4,830,843 A | * | 5/1989 | Usui et al. ................. | 436/326 |
| 4,836,954 A | * | 6/1989 | Rittler ..................... | 237/378 R |
| 5,004,716 A | * | 4/1991 | Ogawa et al. .............. | 423/331 |
| 5,077,248 A | * | 12/1991 | Ogawa et al. .............. | 423/331 |
| 5,302,281 A | * | 4/1994 | Iwamatsu et al. ........... | 208/118 |
| 5,961,816 A | * | 10/1999 | Benazzi et al. ............. | 208/110 |
| 5,997,725 A | * | 12/1999 | Benazzi et al. ............. | 208/110 |
| 6,139,719 A | * | 10/2000 | Benazzi et al. ............. | 208/109 |
| 6,191,333 B1 | * | 2/2001 | Benazzi et al. ............. | 502/63 |
| 6,235,670 B1 | * | 5/2001 | Benazzi et al. ............. | 502/63 |
| 6,251,261 B1 | * | 6/2001 | Kasztelan et al. ......... | 208/111.1 |

FOREIGN PATENT DOCUMENTS

| | | |
|---|---|---|
| EP | 0 523 539 | 1/1993 |
| EP | 0 541 426 | 5/1993 |
| WO | 96/07613 | 3/1996 |
| WO | 96/19289 | 6/1996 |

OTHER PUBLICATIONS

XP-002146076, Synthesis of New Trioctahedral Mg–Smectite, Kazuo Torii et al., Government Industrial Reserach Instutute, Tohoku, Nigatake 4-2-1, Sendai 983, Chemistry Letters, pp. 2021–2024, 1986.
English Abstract of XP-002146068.

* cited by examiner

*Primary Examiner*—Walter D. Griffin
(74) *Attorney, Agent, or Firm*—Millen, White, Zelano & Branigan, P.C.

(57) ABSTRACT

The present invention relates to stevensite or kerolite type trioctahedral phyllosilicates 2:1 containing fluorine, fluorinated in synthesis in an acid medium and modified post-synthesis to bring about Si/Al and/or Mg/Al substitutions which impart acid properties to the solid. These phyllosilicates may be incorporated in the composition of catalysts used to convert hydrocarbons, in particular for hydrocracking.

14 Claims, No Drawings

TRIOCTAHEDRAL PHYLLOSILICATES 2:1 OF A STEVENSITE OR KEROLITE TYPE MODIFIED POST-SYNTHESIS, METHOD OF PREPARATION AND USE IN CATALYSIS

The present invention relates to trioctahedral phyllosilicates 2:1 of the stevensite or kerolite type containing fluoride, fluorinated in synthesis in an acid medium and modified post-synthesis to bring about the Si/Al and/or Mg/Al substitutions which impart acid properties to the solid.

These phyllosilicates may be incorporated in the composition of catalysts used to convert hydrocarbons, in particular for hydrocracking.

Phyllosilicates have a micro- or even meso-pore structure, attributable amongst other things to the nature, number and size of the compensation cations. The variation in the thickness of the space between sheets due to the exchange of compensation cations for other cations causes changes in properties. Phyllosilicates are used for adsorption and catalysis either as an active phase or as a means of assisting the active phase.

Due to the nature of the elements present in the tetrahedral and octahedral cavities and the nature of the compensation cations, the chemical composition of phyllosilicates is also an important factor affecting the selectivity of the exchange of cations, the adsorption selectivity and in particular the catalytic activity. This is explained by the nature and intensity of interactions between their internal and external surfaces on the one hand and with the adsorbed molecules on the other.

Numerous applications, particularly acid catalysis, require proton forms from which compensation cations introduced during synthesis have been completely removed. These forms may be obtained by one or more exchanges of these cations for $NH_4^+$ ions followed by calcination in order to generate the proton form.

Although the chemical bonds between the elements in the structure of phyllosilicates are ion-covalent, they will be assumed to be ionic here in order to simplify the description. Starting from a presentation in which the $O^{2-}$ ions are in one plane, in contact with one another, in the most compact manner, it is possible to obtain a plane having hexagonal cavities, referred to as a hexagonal plane, by removing one $O^{2-}$ ion in two from one of every two rows of $O^{2-}$ ions. The structure of a phyllite may be simply represented using arrangements of hexagonal planes of $O^{2-}$ ions and compact planes of $O^{2-}$ and $OH^-$ ions. The $OH^-$ ions fill the cavities in hexagonal planes of $O^{2-}$ ions. Placing two compact planes one on top of the other bounded on either side by a hexagonal plane enables an octahedral layer (O) to be defined between 2 tetrahedral (T) layers, hence the name TOT sheet. Such an arrangement, also referred to as 2:1, enables a layer of octahedral cavities to be defined, located between two layers of tetrahedral cavities. Each tetrahedron has one $O^{2-}$ ion in common with the octahedral layer and each of the other three $O^{2-}$ ions is shared with another tetrahedron in the same tetrahedral layer.

The crystal lattice is therefore made up of six octahedral cavities having four tetrahedral cavities on either side. If the octahedral sites are occupied by divalent cations, this will be referred to as a trioctahedral phyllosilicate 2:1. In the case of a phyllosilicate made up of the elements Si, Mg, O and the OH group, such an arrangement corresponds to the formula $Si_8Mg_6O_{20}(OH)_4$. The tetrahedral cavities contain the silicon element and the octahedral cavities the magnesium element. Such a formula corresponds to the natural product known as talc.

If a very small fraction of octahedral cavities are unoccupied, a lack of positive charge appears within the structure. This lack of charge will be compensated by the presence of exchangeable compensation cations located in the interlayer space. In the case of a phyllosilicate made up of the elements Si, Mg, O and the OH group, the formula of such a compound may be written as follows for a lattice $$C_{2/zm}{}^{m+}Si_8(Mg_{6-z}\square_z)O_{20}(OH)_4$$

where $\square$ represents an unoccupied octahedral cavity, i.e.

$$Mg_zSi_8(Mg_{6-z}\square_z)O_{20}(OH)_4 \text{ or } Na_{2z}Si_8(Mg_{6-z}\square_z)O_{20}(OH)_4$$

if the exchangeable cation C corresponds to the magnesium or sodium element respectively.

The structural group $[Si_8(Mg_{6-z}\square_z)O_{20}(OH)_4]^{2z-}$ for a lattice or $[Si_4(Mg_{3-z}\square_z)O_{20}(OH)_2]^{2z-}$ for a half lattice corresponds to a natural smectite known as kerolite if z is very close to zero and stevensite if z if higher. Generally speaking, it is not uncommon in the natural product for Mn(II) and Fe(II) ions to be present alongside the magnesium cation in the octahedral cavity.

It is not easy to understand why trioctahedral phyllosilicate 2:1 should be lacking in positive charges in the octahedral layer, currently known under the name of stevensite, as distinct from the products cited in background literature. Its occurrence in nature has been the subject of controversy, because some regard phyllosilicate as a variety of talc. The fact that its chemical composition is close to that of talc goes a long way towards explaining this. Natural stevensite occurs in veins or pockets, mixed to a greater or lesser degree with other phases, which may explain the difficulties encountered when attempting to characterise or sample it. However, progress in the systematic classification of natural phyllosilicates and improved analysis of samples has improved what we know about their characteristics.

Until now, the Si/Al or Mg/Al combination has been produced by synthesis or, in the case of minerals of the smectite type, by a cationic exchange with aluminium in order to adjust the Si/Al and Mg/Al ratios to improve the stability of materials, these exchanges being effected in the absence of any fluoride ion (patent JP 94-191549).

The present invention relates to stevensite or kerolite trioctahedral phyllosilicates 2:1 containing fluorine and having inter-sheet $Mg^{2+}$ cations, fluorinated in synthesis in an acid medium and modified post-synthesis in the presence of fluorine, said post-synthesis fluorination consisting in incorporating aluminium in the structure of the stevensite or kerolite (Mg), i.e. producing a substitution of the silicon and/or magnesium elements by the aluminium. The advantage of this method is that it enables the acidity of the phyllosilicate proposed by the invention to be increased in a controlled manner.

Another objective of the present invention is to propose a method of preparing said phyllosilicates and their use for converting hydrocarbons.

The phyllosilicates proposed by the invention are obtained by processing, post-synthesis, stevensite or kerolite type trioctahedral phyllosilicates 2:1 immediately after synthesis, and these are synthesised in a fluoride medium (for example in the presence of HF acid or any other acid source of fluoride ions and/or any other source of fluoride ions).

The general chemical formula (for a half lattice) of the initial phyllosilicates is as follows:

$$C_{2z/m}{}^{m+}Si_4(Mg_{3-z}\square_z)O_{10}(OH)_{2-u}F_u, nH_2O$$

where
C is the compensation cation from the reaction medium constituted at least partially by the $Mg^{2+}$ cation or a cation introduced by at least one process of post-synthesis ion exchange, selected from the group consisting of the cations of elements from groups IA, IIA and VIII of the periodic table, the cations of rare earths (cations of elements having an atomic number 57 to 71 inclusive), the ammonium cation, organic cations containing nitrogen (among which are alkylammonium and arylammonium), m is the valence of the cation C, z is a number greater than 0 and less than or equal to 1, preferably ranging between 0.01 and 1, u is a number greater than 0 and less than or equal to 1, preferably ranging between 0.01 and 2, n is a real positive number and not zero, and □ stands for an octahedral cavity.

The magnesium element may be partially substituted by at least one of the elements from the group consisting of nickel, cobalt and zinc, these elements being taken from the reaction medium.

The X-ray diffraction diagram of a purely magnesium-based trioctahedral phyllosilicate 2:1 is characterized by the presence of the following rays:

a ray corresponding to a value of $d_{060}$ equal to $1.52 \pm 0.01 \times 10^{-10}$m two other rays corresponding to values of $d_{hkl}$ equal to $4.53 \pm 0.05 \times 10^{-10}$m and $2.56 \pm 0.05 \times 10^{-10}$m at least one reflection 001 such that $d_{001}$ is between 10.1 and $21.5 \times 10^{-10}$m in accordance with the chemical formula of said phyllosilicates. This reflection enables a distinction to be made between trioctahedral phyllosilicate 2:1 of the kerolite type and trioctahedral phyllosilicate 2:1 of the stevensite type. A low value, somewhat less than $11 \times 10^{-10}$m corresponds to trioctahedral phyllosilicate 2:1 of the kerolite type and a highter value, somewhat higher than $11 \times 10^{-10}$m corresponds to trioctahedral phyllosilicate 2:1 of the stevensite type.

Stevensite or kerolite type trioctahedral phyllosilicate 2:1 also exhibits at least one signal during analysis of the fluorine $^{19}F$ by Nuclear Magnetic Resonance with Magic Angle Rotation (NMR-MAR), determined and known by the person skilled in the art. The chemical displacement of this signal depends on the composition of the octahedral layer. The NMR-MAR $^{19}F$ spectrum of stevensite or kerolite type trioctahedral phyllosilicate 2:1 containing magnesium in the octahedral layer is characterised by an intense double signal centred on –175.0 and –176.6 ppm. A breakdown of this signal highlights two shoulders at –178.0 and 181.0 ppm.

The stevensite or kerolite type trioctahedral phyllosilicate 2:1 proposed by the invention is characterised by gaps in the octahedral layer, evidenced by specific swelling properties. In effect, the swelling properties observed on the raw synthesis product disappear after heating for 12 h at 250° C. The X-ray diffraction diagram for stevensite or kerolite type trioctahedral phyllosilicate 2:1 when heated then exhibits a periodicity $d_{001}$ corresponding to that of a talc with an imperfect organisation. Under NMR-MAR analysis of the fluorine $^{19}F$, the probe used in the octahedral layer, the spectrum of the phyllosilicate proposed by the invention and based purely on magnesium, heated to 250° C. for 12 h, will have only one signal centred on –176.6 ppm which can not be broken down. This chemical displacement is attributed to the F(3 Mg) atoms, corresponding to fluorine atoms having three Mg in their environment. The $Mg^{2+}$ cations present as compensation cations have migrated during heating to occupy the gaps in the octahedral position. The product obtained after heating no longer contains compensation cations.

The trioctahedral phyllosilicate 2:1 prepared as proposed by the invention is therefore of the stevensite or kerolite type.

The trioctahedral 2:1 phyllosilicates proposed by the invention are produced from phyllosilicates synthesised in a fluoride medium in the presence of the acid from HF acid or any other acid source of fluoride ions and/or any other source of fluoride ions and having a pH less than or equal to 7, and preferably between 0.5 and 6.5. The presence of the element F enables trioctahedral phyllosilicates 2:1 to be obtained in the absence of alkaline cations. They are then put through a post-synthesis treatment in a fluoride medium in the presence of HF acid or any other acid source of fluoride ions and/or any other source of fluoride ions.

For the purpose of the invention, the general chemical formula (per half lattice) of phyllosilicates containing fluorine, magnesium and aluminium is of the type:

where
C is the compensation cation taken from the reaction medium or a cation introduced by at least one post-synthesis ion exchange process, selected from the group consisting of the cations of elements from groups IA, IIA, IIB and VIII of the periodic table, the cations of rare earths (cations of elements having an atomic number 57 to 71 inclusive), the ammonium cation, the organic cations containing nitrogen (among which are alkylammonium and arylammonium).

m is the valence of the cation C, t is a number ranging between 0 and 3, x is a number greater than 0 and less than or equal to 1, y is a number greater than 0 and less than or equal to 2, z is a number greater than 0 and less than or equal to 2, n is a real positive number and not zero.

The compensation cation is generally magnesium.

The magnesium element may be substituted in part or in full by at least one of the elements from the group consisting of nickel, cobalt and zinc, these elements being taken from the reaction medium.

The X-ray diffraction diagram phyllosilicate 2:1 obtained by the method described above is characterized by the presence of the following rays:

one of more rays corresponding to a value of $d_{060}$ equal to:
$1.52 \pm 0.01 \times 10^{-10}$m, attributable to the trioctahedral character,
$1.50 \pm 0.01 \times 10^{-10}$m, attributable to the di-trioctahedral character,
$1.49 \pm 0.01 \times 10^{-10}$m, attributable to the dioctahedral character, at least one reflection 001 such that $d_{001}$ is between 10.1 and $17.0 \times 10^{-10}$ m in accordance with the chemical formula of said phyllosilicates.

It may also exhibit other rays corresponding to values of $d_{hkl}$ equal to
$4.53 \pm 0.01 \times 10^{-10}$m,
$3.16 \pm 0.01 \times 10^{-10}$m,
$2.56 \pm 0.01 \times 10^{-10}$m
$1.72 \pm 0.01 \times 10^{-10}$m After said post-synthesis treatment with aluminium, the solid proposed by the invention can be characterised under NMR-MAR $^{19}$F analysis by one or two new signals, depending on the processing conditions (duration, temperature, composition of the reaction mixture), centred on −152.0 and −132.0 ppm. These two displacements are attributed to the F(Mg,Al,☐) and F(2A,☐) atoms respectively.

The NMR-MAR of $^{29}$Si enables the tetrahedral layer to be characterised. The spectrum of the stevensite or kerolite, containing only silicon in the tetrahedral layer, is characterised by a signal centred on −95.0 ppm. This chemical displacement is attributed to the Si(3Si) or $Q^3$(0Al) atoms. After post-synthesis treatment with aluminium, the solid proposed by the invention is characterised by one or more signals, depending on the treatment conditions (duration, temperature, composition of the reaction mixture). These new signals are centred on −93.5, −92.6 and −88.1 ppm. These chemical displacements are attributed to Si(3Si) or $Q^3$(0Al) atoms, to Si(2Si, 1 Al) or $Q^3$(1Al) atoms and to Si(1Si, 2Al) or $Q^3$(2Al) atoms. By ascertaining the different contributions, it is then possible to calculate the tetrahedral substitution rate using the formula known to the person skilled in the art. The tetrahedral substitution rate (x) varies depending on the processing duration and temperature.

Finally, the solid proposed by the invention is characterised under NMR-MAR analysis of the aluminium $^{27}$Al by a signal centred on 0 ppm. This chemical displacement is attributed to the aluminium in the tetrahedral layer.

The phyllosilicates obtained after said post-synthesis treatment proposed by the invention have an adjustable acidity which, determined by ammonia adsorption, corresponds to a value in excess of 1.2 m$^2$/100 g of clay calcined at 1000° C. The acidity of the stevensite or kerolite type phyllosilicate prior to post-synthesis modification is less than 0.70 m$^2$/100 g of clay calcined at 1000° C.

The invention also relates to a method of preparing said stevensite or kerolite type trioctahedral phyllosilicates 2:1 proposed by the invention, which consists in:

a) forming a reaction mixture in aqueous solution having a pH less than 7, containing in particular water, at least one source of the silicon element, at least one source of the magnesium element and at least one source of fluorine.

In terms of molar ratio, said mixture has a composition within the following value ranges:

$0 < Mg_{total}/Si \leq 50$, preferably $0 < Mg_{total}/Si \leq 10$, and advantageously at least equal to 0.01, $0 < F^-_{total}/Si \leq 10$, preferably $0 < F^-_{total}/Si \leq 8$, preferably at least equal to 0.01, $0 \leq HF/Si \leq 10$, preferably $0 < HF/Si \leq 8$, preferably at least equal to 0.01, $5 \leq H_2O/Si \leq 500$, preferably $10 \leq H_2O/Si \leq 300$.

$F^-_{total}$ represents the sum of $F^-$ ions from all the fluoride sources and in particular HF acid or any other acid source of fluoride ions and/or any other source of fluoride ions, in particular MgF$_2$ and H$_2$SiF$_6$. Mg$_{total}$ represents the sum of Mg$^{+2}$ ions from all the sources of the magnesium element and optionally MgF$_2$ if MgF$_2$ is used alone or partially as the source of F$^-$ ions. The magnesium source may be mixed with or totally substituted by at least one source of the elements from the group consisting of cobalt, zinc and nickel.

Advantageously, said reaction mixture is prepared so as to have a pH ranging between 0.5 and 7, and preferably between 0.5 and 6.5.

In a preferred approach to preparing trioctahedral phyllosilicates 2:1 as proposed by the invention, the molar ratios of the constituents of the reaction mixture are within the following value ranges:

$0 < Mg_{total}/Si \leq 3$,
$0 < F_{total}/Si \leq 6$,
$0 \leq HF/Si \leq 0.6$,
$40 \leq H_2O/Si \leq 500$.

As an option, it is also possible to work accompanied by stirring and optionally in the presence of seeds of trioctahedral phyllosilicate 2:1 crystals.

The pH of the reaction medium, which is below 7, may be obtained directly using one or more reagents, or by adding an acid.

Numerous sources may be used for the silicon element, which might include, by way of example, silica in the form of hydrogels, aerogels, colloidal suspensions, silica produced by precipitating soluble silicate solutions or by hydrolysis of silica esters such as Si(OC$_2$H$_5$)$_4$, silica prepared by treatments to extract natural or synthetic compounds such as aluminium silicates, aluminosilicates, zeolites.

Among the sources for the magnesium element, for example, it is possible to use the oxide MgO, the hydroxide Mg(OH)$_2$, the salts such as magnesium chloride, fluoride, nitrate and sulphate, organic acid salts. The same types of source may be used for the nickel, cobalt and zinc elements if these partially substitute the magnesium.

Instead of using separate sources for the various elements mentioned above, it would also be possible to use sources combining at least two of the elements.

b) said reaction mixture is maintained at a temperature below 250° C. and preferably below 220° C., preferably in an autoclave, the interior of which is advantageously coated with polytetrafluoroethylene, for a period which may vary from a few hours to a few days depending on the reaction temperature, until a crystallised compound is obtained which is advantageously separated from the parent waters before being washed with distilled water and then dried.

c) the aluminium is incorporated by post-synthesis treatment, by placing the phyllosilicate in stevensite or kerolite form in contact with an aluminium source in the presence of fluorine in an autoclave heated to a temperature ranging between 100 and 250° C. for periods ranging between 2 and 2000 h.

Incorporating the aluminium element in the structure of the stevensite or kerolite(Mg), by bringing about the Si/Al and/or Mg/Al substitutions, enables its acid properties to be enhanced and, by the same token, its catalytic properties for acid catalysis.

The reaction medium is prepared by mixing the various reagents at ambient temperature whilst stirring. The various reagents may be introduced in any order. By preference, they are added in the following order: distilled water, fluorine source, aluminium source and stevensite or kerolite.

Numerous sources may be used for the aluminium element, examples of which are aluminium isopropoxide [Al((CH$_3$)$_2$COH)$_3$] (IsoAl), pseudo-boehmite (AlOOH), preferably pseudo-boehmite. The fluorine sources may be selected from NaF, NH$_4$F and HF.

In a preferred embodiment, after a brief period of curing (several minutes), the mixture is decanted into an autoclave (for example of stainless steel lined with a coating of polytetrafluoroethylene). The autoclave is heated to a temperature ranging between 110 and 170° C. The processing time represents the time during which the autoclave is maintained at temperature and under pressure. It may vary between 2 h and 2000 hours. The autoclave is cooled to ambient temperature. After opening, the solid phase is separated by filtering the liquid phase and is then washed with distilled water and dried.

The octahedral (Mg/Al) and tetrahedral (Si/Al) substitution rates are controlled by acting on the processing temperature and duration.

In order to make it easier to define the composition of the reaction mixture at step c) of post-synthesis modification, the notation system used is as follows:

The theoretical quantity of fluorine needed to expel all the magnesium (octahedral and inter-sheet) contained in the kerolite or stevensite type trioctahedral phyllosilicate 2:1 is written $F_{th}$. It is 0.015 mole for 1 g of phyllosilicate, given that Mg is expelled in the form of $MgF_2$. This value is calculated using the general chemical formula per half-lattice of the phyllosilicate, $C_{2z/m}{}^{m+}Si_4(Mg_{3-z}\square_z)O_{10}(OH)_{2-u}F_u$,n $H_2O$, assuming z=0.

The total quantity of fluorine introduced into the reaction mixture at step c) is written $F_t$.

The theoretical quantity of aluminium needed to ensure that the MG/Al is substituted in full ($3Mg^{2+} \leftrightarrows 2Al^{3+}$), is written $Al_{th}$. It is $5.25 \times 10^{-3}$ mole of aluminium for 1 g of phyllosilicate.

The parameter denoting the molar ratio of the quantity of hydrofluoric acid to the quantity of sodium fluoride and hydrofluoric acid is denoted by:

$$S = \frac{HF}{HF + NaF}$$

a is the ratio $Al/Al_{th}$
f is the ratio $F_t/F_{th}$.
Said reaction mixture corresponding to step c) has a composition such that:
  S is between 0 and 1
  a is between 0 and 30 and more preferably between 2 and 15
  f is between 0 and 1, 0 being excluded,
i.e.
  $Al_2O_3/SiO_2$: 0.3 to 5,
  $H_2O/SiO_2$: 140 to 265,
  $F_t/SiO_2$: 0 to 2 (0 excluded)
and, if HF and/or NaF is used:
  $HF/SiO_2$: 0 to 2,
  $NaF/SiO_2$: 0 to 2, $$\frac{HF}{HF + NaF} = 0 \text{ to } 1.$$

Surprisingly, the quantity of fluorine introduced into the reaction mixture has been found to affect the tetrahedral substitution rate (x) and the octahedral substitution rate (y). If using the sodium fluoride alone, the results obtained are close to those obtained using hydrofluoric acid alone. However, sodium fluoride enables a higher rate of tetrahedral substitution to be obtained.

If two fluoride sources are used, the tetrahedral substitution rate (x) varies randomly depending on the HF/NaF+HF ratio, the total quantity of fluorine being maintained constant. The HF/NaF+HF ratio, on the other hand, has a surprising effect on the octahedral substitution rate.

The trioctahedral phyllosilicates 2:1 proposed by the invention may be used alone or as a mixture with a matrix, such as catalysts used to convert hydrocarbons, in particular for hydrocracking.

The matrices used are usually selected from the group consisting of alumina, silica, magnesia, titanium oxide, zirconium, combinations at least two of these compounds and the alumina-boron oxide combinations.

The matrix is preferably selected from the group consisting of silica, alumina, magnesia, silica-alumina mixtures and silica-magnesia mixtures.

The catalyst will then have a content by weight of stevensite or kerolite type trioctahedral phyllosilicate 2:1 proposed by the invention which is advantageously in the range of between 10 and 99.5%.

The catalyst containing the phyllosilicate proposed by the invention will additionally contain a hydrogenating or dehydrogenating function, generally constituted by at least one metal and/or metal compound selected from groups IA, VIB and VIII of the periodic table, for example platinum, palladium and/or nickel.

For hydrocracking applications, the charges used in the method are, for example, gas oils, gas oils under vacuum, residues with the asphalt removed or hydro-treated or equivalent. These may be heavy cuts constituted by at least 80% by volume of compounds whose boiling point is in excess of 350° C. and preferably less than 580° C. They generally contain heteroatoms such as sulphur and nitrogen. The nitrogen content is usually between 1 and 5000 ppm by weight and the sulphur content between 0.01 and 5% by weight. The hydrocracking conditions such as temperature, pressure, hydrogen recycling rates, hourly velocity by volume, may vary depending on the nature of the charge, the quality of the desired products and the installations used by the refiner.

Temperatures are generally in excess of 230° C. and commonly between 300° C. and 480° C., preferably less than 450° C. The pressure is greater than or equal to 2 MPa and in general higher than 3 MPa, even 10 MPa. The hydrogen recycling rate is a minimum of 100 and commonly between 260 and 3000 liters of hydrogen per liter of charge. The hourly velocity by volume is generally between 0.2 and 10 $h^{-1}$.

The following examples illustrate the invention but without limiting its scope.

EXAMPLE NO. 1

Synthesis of Trioctahedral Phyllosilicate 2:1 of the Kerolite Type

The following are added to 86.4 g of distilled water in succession and as specified:
  0.8 g of 5% HF acid made up as a 40% dilution of the commercially available solution (Fluka)
  4.1 g of magnesium acetate $Mg(CH_3COO)_2$, $4H_2O$ (Prolabo), accompanied by vigorous stirring,
  1.5 g of powdered silicon oxide ($SiO_2$), Aerosil 130 from Degussa) accompanied by moderate stirring.

The molar composition of the hydrogel thus prepared, relative to one mole of oxide $SIO_2$ is:
  1.0 $SiO_2$; 0.75 MgO; 0.08 HF; 192 $H_2O$
i.e., in terms of molar ratio
  Mg/Si=0.75
  $F^-$/Si=0.08
  $H_2O/SiO_2$=192.

This composition does not take account of the water contributed by the magnesium source and HF acid.

The hydrogel thus obtained is cured for 2 hours at ambient temperature accompanied by moderate stirring. The pH is close to 5.5. Crystallisation then takes place in a steel autoclave with a coating of PTFE having a 120 ml capacity at 220° C. under autogenous pressure for 48 hours and without stirring. The autoclave is then cooled by quenching.

The product is recovered, filtered and thoroughly washed with distilled water. The pH of the parent waters is in the order of 4. The product is dried for 48 hours at 60° C. The mass recovered is close to 2.1 g.

At the end of these 48 hours, the product obtained is placed in a desiccator containing a saturated solution of $NH_4Cl$ with $P/P_0=0.80$ for 3 days. After these 3 days, the product is characterised by means of its X-ray diffraction diagram.

The reading is taken at ambient temperature and at a relative humidity P/P0 of 0.80.

having a 120 ml capacity at 170° C. under autogenous pressure for 168 hours without stirring. The autoclave is then cooled by quenching.

The product is recovered, filtered and thoroughly washed with distilled water. The pH of the parent waters is in the order of 4. It is dried for 24 hours at 60° C. The mass recovered is close to 1.7 g.

Characterising the silicon $^{29}Si$, aluminium $^{27}Al$ and the fluorine $^{19}F$ by Nuclear Magnetic Resonance with a Magic Angle Rotation (NMR-MAR) will determine the substitutions. The references used are $Si(CH_3)_4$ for the silicon, $CFCl_3$ for the fluorine and $(Al(H_2O)_6)^{3+}$ for the aluminium.

|  | $^{29}Si$ | | $^{27}Al$ | | $^{19}F$ | | |
| --- | --- | --- | --- | --- | --- | --- | --- |
| Chemical displacement (ppm) | −88.1 | −92.6 | 60 | 0 | −176.6 | −152.0 | −132.0 |
| Attribution | $Q^3(1Al)$ | $Q^3(0Al)$ | $Al_{out}$ | $Al_{tetra}$ | F(3Mg) | F(Mg,Al,□) | F(2 Al,□) |

| $d_{hkl}/10^{-10}m$ | relative I |
| --- | --- |
| 10.7 | 63.0 |
| 4.54 | 100.0 |
| 3.17 | 17.0 |
| 2.60 | 53.0 |
| 1.72 | 19.0 |
| 1.52 | 83.0 |

The total acidity determined by thermo-adsorption of ammonia is 0.70 m²/100 g of clay calcined at 1000° C.

EXAMPLE NO. 2

Post-Synthesis Modification of a Kerolite Type Trioctahedral Phyllosilicate 2:1

The following are added to 50.0 g of distilled water in succession and as specified:

6.28 g of 5% HF acid made up as a 40% dilution of the commercially available solution (Fluka)

0.79 g of pseudo-boehmite (AlOOH, 69% Catapal B (Vista)), with vigorous stirring, 1.0 g of kerolite fluorinated in synthesis in an acid medium as stipulated in example 1, with moderate stirring.

In terms of molar ratio, the molar composition of the hydrogel thus prepared, relative to one mole of oxide $SiO_2$ is:

$H_2O/SiO_2=265$,
 $F_t/SiO_2=1.5$,
 $HF/SiO_2=2$,
 $NaF/SiO_2=0$,
 $HF/HF+NaF=1$,
 $F_t/F_{th}=1$,
 $Al_2O_3/SiO_2=1$.

This composition does not take account of the water contributed by the aluminium source, the fluoride and the phyllosilicate.

The mixture is stirred moderately at ambient temperature for several minutes. The pH is close to 2. The processing then takes place in a steel autoclave with a coating of PTFE The BET specific surface area is 123±1 m²/g.

The total acidity determined by thermo-adsorption of ammonia is 1.65 m²/100 g of clay calcined at 1000° C.

The tetrahedral substitution rate x is 0.20.

EXAMPLE NO. 3

Post-Synthesis Modification of a Kerolite Type Trioctahedral Phyllosilicate 2:1

The following are added to 50.0 g of distilled water in succession as specified:

0.67 g of sodium fluoride (NaF, >99%, Fluka)

0.79 g of pseudo-boehmite (AlOOH, 69% Catapal B, Vista), with vigorous stirring, 1.0 g of kerolite fluorinated in synthesis in an acid medium as stipulated in example 1, with moderate stirring.

In terms of molar ratio, the molar composition of the hydrogel thus prepared, relative to one mole of oxide $SiO_2$, is:

$H_2O/SiO_2=265$,
 $F_t/SiO_2=1.5$,
 $HF/SiO_2=0$,
 $NaF/SiO_2=1$,
 $HF/HF+NaF=0$,
 $F_t/F_{th}=1$,
 $Al_2O_3/SiO_2=1$.

This composition does not take account of the water contributed by the aluminium and fluoride source and the stevensite or kerolite phyllosilicate.

The mixture is stirred moderately at ambient temperature. The pH is close to 9. The processing then takes place in a steel autoclave with a coating of PTFE having a 120 ml capacity at 170° C. under autogenous pressure for 168 hours without stirring. The autoclave is then cooled by quenching.

The product is recovered, filtered and thoroughly washed with distilled water. The pH of the parent waters is in the order of 6. It is dried for 24 hours at 60° C. The mass recovered is close to 1.7 g.

Characterising the silicon $^{29}Si$, aluminium $^{27}Al$ and the fluorine $^{19}F$ by Nuclear Magnetic Resonance with a Magic Angle Rotation (NMR-MAR) will determine the substitutions. The references used are $Si(CH_3)_4$ for the silicon, $CFCl_3$ for the fluorine and $(Al(H_2O)_6)^{3+}$ for the aluminium.

|  | $^{29}Si$ | | $^{27}Al$ | | $^{19}F$ | | |
|---|---|---|---|---|---|---|---|
| Chemical displacement (ppm) | −88.1 | −93.6 | 60 | 0 | −176.6 | −152.0 | −132.0 |
| Attribution | $Q^3$(1Al) | $Q^3$(0Al) | $Al_{out}$ | $Al_{tetra}$ | F(3Mg) | F(Mg,Al,☐) | F(2 Al,☐) |

The BET specific surface area is 106±1 m²/g.
The tetrahedral substitution rate x is 0.43.

EXAMPLE NO. 4

Post-Synthesis Modification of a Kerolite Type Trioctahedral Phyllosilicate 2:1

The following are added to 50.0 g of distilled water in succession and as specified:

- 5.0 g of 5% HF acid made up as a 40% dilution of the commercially available solution (Fluka)
- 0.13 g of sodium fluoride (NaF, >99%, Fluka)
- 0.79 g of pseudo-boehmite (AlOOH, 69% Catapal B, Vista), with vigorous stirring,
- 1.0 g of kerolite fluorinated in synthesis in an acid medium as stipulated in example 1, with moderate stirring.

In terms of molar ratio, the molar composition of the hydrogel thus prepared, relative to one mole of oxide $SiO_2$ is:

$H_2O/SiO_2=265$,
$F_t/SiO_2=1.5$,
$HF/SiO_2=1.2$,
$NaF/SiO_2=0.3$,
$HF/HF+NaF=0.8$,
$F_t/F_{th}=1$,
$Al_2O_3/SiO_2=1$.

This composition does not take account of the water contributed by the aluminium and fluoride sources and the phyllosilicate.

The mixture is stirred moderately at ambient temperature. The pH is close to 3. The processing then takes place in a steel autoclave with a coating of PTFE having a 120 ml capacity at 170° C. under autogenous pressure for 168 hours without stirring. The autoclave is then cooled by quenching.

The product is recovered, filtered and thoroughly washed with distilled water. The pH of the parent waters is in the order of 7.5. It is dried for 24 hours at 60° C. The mass recovered is close to 1.7 g.

Characterising the silicon $^{29}Si$, aluminium $^{27}Al$ and the fluorine $^{19}F$ by Nuclear Magnetic Resonance with a Magic Angle Rotation (NMR-MAR) will determine the substitutions. The references used are $Si(CH_3)_4$ for the silicon, $CFCl_3$ for the fluorine and $(Al(H_2O)_6)^{3+}$ for the aluminium.

The BET specific surface area is 127±2 m²/g.
The tetrahedral substitution rate x is 0.35.

EXAMPLE NO. 5

Post-Synthesis Modification of a Kerolite Type Trioctahedral Phyllosilicate 2:1

The following are added to 449 g of distilled water in succession and as specified:

- 50.0 g of 5% HF acid made up as a 40% dilution of the commercially available solution (Fluka)
- 1.3 g of sodium-fluoride (NaF, >99%, Fluka).
- 7.3 g of pseudo-boehmite (AlOOH, 75.6% Pural, Condea), with vigorous stirring,
- 10.0 g of kerolite fluorinated in synthesis in an acid medium as stipulated in example 1, with moderate stirring.

In terms of molar ratio, the molar composition of the hydrogel thus prepared, relative to one mole of oxide $SiO_2$ is:

$H_2O/SiO_2=265$,
$F_t/SiO_2=1.5$,
$HF/SiO_2=1.2$,
$NaF/SiO_2=0.3$,
$HF/HF+NaF=0.8$,
$F_t/F_{th}=1$,
$Al_2O_3/SiO_2=1$.

This composition does not take account of the water contributed by the aluninium and fluoride sources and the phyllosilicate.

The mixture is stirred moderately at ambient temperature. The pH is close to 4. The processing then takes place in a steel autoclave with a coating of PTFE having a 1000 ml capacity at 170° C. under autogenous pressure for 168 hours and without agitation. The autoclave is then cooled by quenching.

The product is recovered, filtered and thoroughly washed with distilled water. The pH of the parent waters is in the order of 4.5. It is dried for 24 hours at 60° C. The mass recovered is close to 12.5 g.

Characterising the silicon $^{29}Si$, aluminium $^{27}Al$ and the fluorine $^{19}F$ by Nuclear Magnetic Resonance with a Magic Angle Rotation (NMR-MAR) will determine the substitutions. The references used are $Si(CH_3)_4$ for the silicon, $CFCl_3$ for the fluorine and $(Al(H_2O)_6)^{3+}$ for the aluminium.

|  | $^{29}Si$ | | $^{27}Al$ | | $^{19}F$ | | |
|---|---|---|---|---|---|---|---|
| Chemical displacement (ppm) | −88.1 | −92.6 | 60 | 0 | −176.6 | −152.0 | −132.0 |
| Attribution | $Q^3$(1Al) | $Q^3$(0Al) | $Al_{out}$ | $Al_{tetra}$ | F(3Mg) | F(Mg,Al,☐) | F(2 Al,☐) |

| | $^{29}Si$ | | $^{27}Al$ | | $^{19}F$ | | |
|---|---|---|---|---|---|---|---|
| Chemical displacement (ppm) | −88.1 | −92.6 | 60 | 0 | −176.6 | −152.0 | −132.0 |
| Attribution | $Q^3$(1Al) | $Q^3$(0Al) | $Al_{out}$ | $Al_{tetra}$ | F(3Mg) | F(Mg,Al,□) | F(2 Al,□) |

The tetrahedral substitution rate x is 0.33.

EXAMPLE NO. 6

Post-Synthesis Modification of a Kerolite Type Trioctahedral Phyllosilicate 2:1

The following are added to 50 g of distilled water in succession and as specified:

- 5.0 g of 5% HF acid made up as a 40% dilution of the commercially available solution (Fluka)
- 0.13 g of sodium fluoride (NaF, >99%, Fluka).
- 2.31 g of aluminium isopropoxide $(Al(CH_3)_2COH)_3$, 98%, Aldrich), with vigorous stirring,
- 1.0 g of kerolite fluorinated in synthesis in an acid medium as stipulated in example 1, with moderate stirring.

In terms of molar ratio, the molar composition of the hydrogel thus prepared, relative to one mole of oxide $SiO_2$ is:

$H_2O/SiO_2$=265,
$F_t/SiO_2$=1.5,
$HF/SiO_2$=1.2,
$NaF/SiO_2$=0.3,
$HF/HF+NaF$=0.8,
$F_t/F_{th}$=1,
$Al_2O_3/SiO_2$=1.

This composition does not take account of the water contributed by the aluminium and fluoride sources and the phyllosilicate.

The mixture is stirred moderately at ambient temperature. The pH is close to 5. The processing then takes place in a steel autoclave with a coating of PTFE having a 120 ml capacity at 170° C. under autogenous pressure for 168 hours without stirring. The autoclave is then cooled by quenching.

The product is recovered, filtered and thoroughly washed with distilled water. The pH of the parent waters is in the order of 5. It is dried for 24 hours at 60° C. The mass recovered is close to 1.1 g.

Characterising the silicon $^{29}Si$, aluminium $^{27}Al$ and the fluorine $^{19}F$ by Nuclear Magnetic Resonance with a Magic Angle Rotation (NMR-MAR) will determine the substitutions. The references used are $Si(CH_3)_4$ for the silicon, $CFCl_3$ for the fluorine and $(Al(H_2O)_6)^{3+}$ for the aluminium.

The BET specific surface area is 118±2 $m^2/g$.
The total acidity is 1.57 $m^2q/100$ g of clay calcined at 1000° C.
The tetrahedral substitution rate x is 0.05.

EXAMPLE NO. 7

Post-Synthesis Modification of a Kerolite Type Trioctahedral Phyllosilicate 2:1

The following are added to 50 g of distilled water in succession as specified:

- 4.0 g of 5% HF acid made up as a 40% dilution of the commercially available solution (Fluka)
- 0.24 g of sodium fluoride (NaF, >99%, Fluka).
- 0.73 g of pseudo-boehmite (AlOOH, 75.6% Pural, Condea), with vigorous stirring,
- 1.0 g of kerolite fluorinated in synthesis in an acid medium as stipulated in example 1, with moderate stirring.

In terms of molar ratio, the molar composition of the hydrogel thus prepared, relative to one mole of oxide $SiO_2$ is:

$H_2O/SiO_2$=265,
$F_t/SiO_2$=1.5,
$HF/SiO_2$=0.95,
$NaF/SiO_2$=0.54,
$HF/HF+NaF$=0.64,
$F_t/F_{th}$=1,
$Al_2O_3/SiO_2$=1.

This composition does not take account of the water contributed by the aluminium and fluoride sources and the phyllosilicate.

The mixture is stirred moderately at ambient temperature. The pH is close to 5. The processing then takes place in a steel autoclave with a coating of PTFE having a 120 ml capacity at 150° C. under autogenous pressure for 336 hours without stirring. The autoclave is then cooled by quenching.

The product is recovered, filtered and thoroughly washed with distilled water. The pH of the parent waters is in the order of 7. It is dried for 24 hours at 60° C. The mass recovered is close to 1.8 g.

Characterising the silicon $^{29}Si$, aluminium $^{27}Al$ and the fluorine $^{19}F$ by Nuclear Magnetic Resonance with a Magic

| | $^{29}Si$ | | $^{27}Al$ | | $^{19}F$ | | |
|---|---|---|---|---|---|---|---|
| Chemical displacement (ppm) | −88.1 | −92.6 | 60 | 0 | −176.6 | −152.0 | −132.0 |
| Attribution | $Q^3$(1Al) | $Q^3$(0Al) | $Al_{out}$ | $Al_{tetra}$ | F(3Mg) | F(Mg,Al,□) | F(2 Al,□) |

Angle Rotation (NMR-MAR) will determine the substitutions. The references used are $Si(CH_3)_4$ for the silicon, $CFCl_3$ for the fluorine and $(Al(H_2O)_6)^{3+}$ for the aluminium.

| | $^{29}Si$ | | $^{27}Al$ | | $^{19}F$ | |
|---|---|---|---|---|---|---|
| Chemical displacement (ppm) | −88.1 | −93.5 | 60 | 0 | −176.0 | −152.0 |
| Attribution | $Q^3(1Al)$ | $Q^3(0Al)$ | $Al_{oct}$ | $Al_{tetra}$ | F(3Mg) | F(Mg,Al,☐) |

The tetrahedral substitution rate x is 0.50.

EXAMPLE NO. 8

Post-Synthesis Modification of a Kerolite Type Trioctahedral Phyllosilicate 2:1

The following are added to 50 g of distilled water in succession and as specified:

5.0 g of 5% HF acid made up as a 40% dilution of the commercially available solution (Fluka)

0.13 g of sodium fluoride (NaF, >99%, Fluka).

0.73 g of pseudo-boehmite (AlOOH, 75.6% Pural, Condea), with vigorous stirring, 1.0 g of kerolite fluorinated in synthesis in an acid medium as stipulated in example 1, with moderate stirring.

In terms of molar ratio, the molar composition of the hydrogel thus prepared, relative to one mole of oxide $SiO_2$ is:

$H_2O/SiO_2=265$,
$F^-_t/SiO_2=1.5$,
$HF/SiO_2=1.2$,
$NaF/SiO_2=0.3$,
$HF/HF+NaF=0.8$,
$F_t/F_{th}=1$,
$Al_2O_3/SiO_2=1$.

This composition does not take account of the water contributed by the aluminium and fluoride sources and the phyllosilicate.

The mixture is stirred moderately at ambient temperature. The pH is close to 5. The processing then takes place in a steel autoclave with a coating of PTFE having a 120 ml capacity at 170° C. under autogenous pressure for 16 hours without stirring. The autoclave is then cooled by quenching.

The product is recovered, filtered and thoroughly washed with distilled water. The pH of the parent waters is in the order of 7. It is dried for 24 hours at 60° C. The mass recovered is close to 1.8 g.

Characterising the silicon $^{29}Si$, aluminium $^{27}Al$ and the fluorine $^{19}F$ by Nuclear Magnetic Resonance with a Magic Angle Rotation (NMR-MAR) will determine the substitutions. The references used are $Si(CH_3)_4$ for the silicon, $CFCl_3$ for the fluorine and $(Al(H_2O)_6)^{3+}$ for the aluminium.

| | $^{29}Si$ | | | | $^{19}F$ | |
|---|---|---|---|---|---|---|
| Chemical displacement (ppm) | −88.1 | −92 | −93.5 | −95.0 | −176.0 | −152.0 |
| Attribution | $Q^3(1Al)$ | $Q^3(0Al)$ | $Q^3(0Al)$ | Si(3Si)Mg | F(3Mg) | F(Mg,Al,☐) |

The tetrahedral substitution rate x is 0.14.

EXAMPLE NO. 9

Post-Synthesis Modification in the Absence of Fluorine

The following are added to 50 g of distilled water in succession and as specified:

0.73 g of pseudo-boehmite (AlOOH, 75.6% Pural, Condea), with vigorous stirring, 1.0 g of kerolite fluorinated in synthesis in an acid medium as stipulated in example 1, with moderate stirring.

In terms of molar ratio, the molar composition of the hydrogel thus prepared, relative to one mole of oxide $SiO_2$ is:

$H_2O/SiO_2=265$,
$F^-_t/SiO_2=0$,
$HF/SiO_2=0$,
$NaF/SiO_2=0$,
$HF/HF+NaF=0$,
$F_t/F_{th}=1$,
$Al_2O_3/SiO_2=1$.

This composition does not take account of the water contributed by the aluminium and fluoride sources and the phyllosilicate.

The mixture is stirred moderately at ambient temperature. The pH is close to 6. The processing then takes place in a steel autoclave with a coating of PTFE having a 120 ml capacity at 170° C. under autogenous pressure for 168 hours without stirring. The autoclave is then cooled by quenching.

The product is recovered, filtered and thoroughly washed with distilled water. The pH of the parent waters is in the order of 4.5. It is dried for 24 hours at 60° C. The mass recovered is close to 0.8 g.

Characterising the silicon $^{29}Si$, aluminium $^{27}Al$ and the fluorine $^{19}F$ by Nuclear Magnetic Resonance with a Magic Angle Rotation (NMR-MAR) will determine the substitutions. The references used are $Si(CH_3)_4$ for the silicon, $CFCl_3$ for the fluorine and $(Al(H_2O)_6)^{3+}$ for the aluminium.

| | $^{29}Si$ | $^{19}F$ |
|---|---|---|
| Chemical displacement (ppm) | −95.0 | −176.0 |
| Attribution | $Q^3(0Al)$ | F(3Mg) |

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/16.382, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A crystallized phyllosilicate having:
a) the general chemical formula (per half-lattice)

$C_{(2(3-t-y)+x-y)/m}{}^{m+}(Si_{4-x}Al_x)(Mg_tAl_y\square_{3-t-y})O_{10}(OH)_{2-z}F_z,nH_2O$ where
- $\square$ represents an unoccupied octahedral cavity,
- C is the compensation cation taken from a reaction medium or a cation introduced by at least one post-synthesis ion exchange process, selected from the group consisting of the cations of elements from groups IA, IIA, and VIII of the periodic table, the cations of rare earth elements having an atomic number of 57 to 71 inclusive, the ammonium cation and, the organic cations containing nitrogen,
- m is the valence of the cation C,
- t is a number ranging between 0 and 3,
- x is a number greater than 0 and less than or equal to 1,
- y is a number greater than 0 and less than or equal to 2,
- z is a number greater than 0 and less than or equal to 2,
- n is a real positive number and not zero, and b) an X-ray diffraction diagram characterized by the presence of the following rays:
one or more rays corresponding to a value of $d_{060}$ equal to:
- $1.52\pm0.01\times10^{-10}$m, attributable to the trioctahedral character,
- $1.50\pm0.01\times10^{-10}$m, attributable to the di-trioctahedral character,
- $1.49\pm0.01\times10^{-10}$m, attributable to the dioctahedral character, and at least one reflection 001 such that $d_{001}$ is between 10.1 and $17.0\times10^{-10}$m.

2. A phyllosilicate as claimed in claim 1 wherein the magnesium is partially replaced by at least one of the elements selected from the group consisting of cobalt, nickel and zinc.

3. Method of preparing phyllosilicates as claimed in claim 1 which comprises:
a) forming a reaction mixture in aqueous solution having a pH less than 7, containing water, at least one source of the silicon element, at least one source of magnesium element and at least one source of fluorine, including from HF and/or NaF, said mixture having a composition, in terms of molar ratio, within the following value ranges:

$0<Mg_{total}/Si\leq50$
$0<F^-_{total}/Si\leq10$
$0\leq HF_{total}/Si\leq10$
$5\leq H_2O/Si\leq500$ where $F^-_{total}$ represents the sum of $F^-$ ions from all sources of the fluoride ion and $Mg_{total}$ represents the sum of $Mg^{+2}$ ions from al the sources of magnesium, b) said reaction mixture is maintained at a temperature below 250° C., c) the aluminium is incorporated by post-synthesis treatment, by placing the phyllosilicate obtained in contact with an aluminium source in the presence of fluorine in an autoclave heated to a temperature of 100–250° C. for periods ranging between 2 and 2000 h, the molar ratios of the constituents of the reaction mixture for this step being within the ranges of the following values:

$Al_2O_3/SiO_2$: 0.3 to 5,
$H_2O/SiO_2$: 140 to 265,
$F_t/SiO_2$: more than 0 to 2
and, if HF and br NaF is used:
$HF/SiO_2$: 0 to 2,
$NaF/SiO_2$: 0 to 2, and $$\frac{HF}{HF+NaF} = 0 \text{ to } 1.$$

4. A method of preparing phyllosilicates as claimed in claim 3, in which, at step a), said reaction mixture has a composition, in terms of molar ratio, in the ranges:

$0<Mg_{total}/Si\leq10$,
$0<F^-_{total}/Si\leq8$,
$0\leq HF/Si\leq8$,
$40\leq H_2O/Si\leq300$.

5. A method of preparing phyllosilicates as claimed in claim 3, in which, at step a), said reaction mixture has a composition, in terms of molar ratio, in the ranges:

$0<Mg_{total}/Si\leq3$,
$0<F^-_{total}/Si\leq6$,
$0\leq HF/Si\leq0.6$,
$40\leq H_2O/Si\leq500$.

6. A method as claimed in claim 4, in which the magnesium source may be mixed with at least one source of the elements from the group consisting of cobalt, zinc and nickel.

7. A catalyst containing phyllosilicate as claimed in claim 1.

8. Catalyst as claimed in claim 7, containing at least one matrix being chosen from the group consisting of alumina, silica, magnesia, titanium oxide, zirconium oxide, boron oxide.

9. A catalyst containing a phyllosilicate as claimed in claim 7 containing at least one element chosen from the group consisting of the elements in groups IA, VIB and VIII.

10. In a process comprising hydrocracking hydrocarbons in contact with a catalyst, the improvement wherein the catalyst is a catalyst according to claim 7.

11. In a process comprising hydrocracking hydrocarbons in contact with a catalyst, the improvement wherein the catalyst is a catalyst according to claim 8.

12. In a process comprising hydrocracking hydrocarbons in contact with a catalyst, the improvement wherein the catalyst is a catalyst according to claim 9.

13. A catalyst comprising a phyllosilicate prepared by the method of claim 3.

14. The method of claim 3, wherein the reaction mixture has a pH of between 0.5 and 6.5.

* * * * *